(12) United States Patent
Randolph et al.

(10) Patent No.: US 10,695,225 B2
(45) Date of Patent: *Jun. 30, 2020

(54) SUPER-ABSORBENT, REDUCED-PRESSURE WOUND DRESSINGS AND SYSTEMS

(71) Applicant: KCI Licensing, Inc., San Antonio, TX (US)

(72) Inventors: Larry Tab Randolph, San Antonio, TX (US); Justin Alexander Long, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 450 days.

This patent is subject to a terminal disclaimer.

(21) Appl. No.: 14/309,705

(22) Filed: Jun. 19, 2014

(65) Prior Publication Data

US 2014/0303578 A1 Oct. 9, 2014

Related U.S. Application Data

(60) Continuation of application No. 13/546,161, filed on Jul. 11, 2012, now Pat. No. 8,795,244, which is a
(Continued)

(51) Int. Cl.
*A61F 13/00* (2006.01)
*A61F 13/02* (2006.01)
(Continued)

(52) U.S. Cl.
CPC .. *A61F 13/00059* (2013.01); *A61F 13/00017* (2013.01); *A61F 13/00029* (2013.01);
(Continued)

(58) Field of Classification Search
CPC ......... A61M 1/00; A61M 27/00; A61L 15/16; A61F 13/02; A61F 13/15;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

English translation of specification for DE 4328190 A (Achtenberg et al).*
(Continued)

*Primary Examiner* — Kai H Weng

(57) ABSTRACT

A super-absorbent dressing assembly for use with a reduced-pressure wound treatment system includes a breathable, fluid restricted dry layer for placement against a wound, a super-absorbent layer, and a non-breathable layer, and a drape extending over the non-breathable layer. A reduced-pressure interface is available to fluidly couple the super-absorbent layer to a reduced-pressure subsystem. The super-absorbent dressing assembly preferably supplies a compressive force when placed under reduced pressure. A reduced-pressure treatment system uses a super-absorbent bolster to treat wounds, e.g., linear wounds.

20 Claims, 3 Drawing Sheets

Related U.S. Application Data division of application No. 12/475,285, filed on May 29, 2009, now Pat. No. 8,241,261.

(60) Provisional application No. 61/144,067, filed on Jan. 12, 2009, provisional application No. 61/121,362, filed on Dec. 10, 2008, provisional application No. 61/057,810, filed on May 30, 2008, provisional application No. 61/057,808, filed on May 30, 2008, provisional application No. 61/057,807, filed on May 30, 2008, provisional application No. 61/057,805, filed on May 30, 2008, provisional application No. 61/057,803, filed on May 30, 2008, provisional application No. 61/057,802, filed on May 30, 2008, provisional application No. 61/057,800, filed on May 30, 2008, provisional application No. 61/057,798, filed on May 30, 2008, provisional application No. 61/057,797, filed on May 30, 2008.

(51) Int. Cl.
*A61L 15/60* (2006.01)
*A61M 1/00* (2006.01)
*A61H 1/00* (2006.01)
*A61F 15/00* (2006.01)

(52) U.S. Cl.
CPC .. *A61F 13/00034* (2013.01); *A61F 13/00038* (2013.01); *A61F 13/00068* (2013.01); *A61F 13/022* (2013.01); *A61F 13/0209* (2013.01); *A61F 13/0216* (2013.01); *A61F 13/0223* (2013.01); *A61F 13/0243* (2013.01); *A61F 13/0289* (2013.01); *A61F 15/008* (2013.01); *A61H 1/008* (2013.01); *A61L 15/60* (2013.01); *A61M 1/0023* (2013.01); *A61M 1/0088* (2013.01); *H05K 999/99* (2013.01); *A61F 13/00* (2013.01); *A61F 2013/0028* (2013.01); *A61F 2013/0054* (2013.01); *A61F 2013/00131* (2013.01); *A61F 2013/00136* (2013.01); *A61F 2013/00174* (2013.01); *A61F 2013/00182* (2013.01); *A61F 2013/00246* (2013.01); *A61F 2013/00536* (2013.01); *A61F 2013/00748* (2013.01); *A61M 2205/70* (2013.01); *A61M 2207/00* (2013.01); *A61M 2210/1007* (2013.01); *A61M 2210/1021* (2013.01); *Y10T 29/49* (2015.01); *Y10T 29/49826* (2015.01)

(58) Field of Classification Search
CPC .......... A61F 13/00059; A61F 13/00017; A61F 13/00029; A61F 13/00034; A61F 13/00038; A61F 13/00068; A61F 13/0209; A61F 13/0216; A61F 13/022; A61F 13/0243; A61F 13/0289
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |

(56) References Cited

U.S. PATENT DOCUMENTS

| | | | |
|---|---|---|---|
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0007014 | A1* | 1/2002 | Hyde ............ A61L 15/585 525/191 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2003/0040691 | A1* | 2/2003 | Griesbach, III .... A61F 13/0273 602/45 |
| 2006/0079852 | A1 | 4/2006 | Bubb et al. |
| 2007/0185426 | A1 | 8/2007 | Ambrosio et al. |
| 2008/0071207 | A1* | 3/2008 | de Luis ............ A61F 13/00017 602/47 |
| 2014/0163491 | A1 | 6/2014 | Schuessler et al. |
| 2015/0080788 | A1 | 3/2015 | Blott et al. |

FOREIGN PATENT DOCUMENTS

| | | |
|---|---|---|
| AU | 755496 | 2/2002 |
| CA | 2005436 | 6/1990 |
| CN | 1545991 A | 11/2004 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/01173 | 1/1999 |
| WO | 99/13793 | 3/1999 |
| WO | 0185248 A1 | 11/2001 |
| WO | 2007030601 | 3/2004 |
| WO | 2007085396 A1 | 8/2007 |

OTHER PUBLICATIONS

Extended European Search Report correspdonding to Application No. 171645070, dated Jul. 18, 2017.

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (copy and certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

(56) References Cited

OTHER PUBLICATIONS

Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

* cited by examiner

SUPER-ABSORBENT, REDUCED-PRESSURE WOUND DRESSINGS AND SYSTEMS

RELATED APPLICATIONS

This application is a continuation of U.S. patent application Ser. No. 13/546,161 filed Jul. 11, 2012 which is a divisional of U.S. patent application Ser. No. 12/475,285 filed May 29, 2009, now U.S. Pat. No. 8,241,261, which claims the benefit, under 35 U.S.C. § 119(e), of the filing of U.S. Provisional Patent Application Ser. No. 61/057,807, entitled "Reduced-pressure Surgical Wound Treatment System," filed May 30, 2008; U.S. Provisional Patent Application Ser. No. 61/057,798, entitled "Dressing Assembly For Subcutaneous Wound treatment Using Reduce Pressure," filed May 30, 2008; U.S. Provisional Patent Application Ser. No. 61/057,808, entitled "See-Through, Reduced-Pressure Dressing," filed May 30, 2008; U.S. Provisional Patent Application Ser. No. 61/057,802, entitled "Reduced-Pressure Dressing Assembly For Use in Applying a Closing Force," filed May 30, 2008; U.S. Provisional Patent Application Ser. No. 61/057,803, entitled "Reduced-Pressure, Linear-Wound Treatment System," filed May 30, 2008; U.S. Provisional Patent Application Ser. No. 61/057,800, entitled "Reduced-Pressure, Compression System and Apparatus for use on a Curved Body Part," filed, May 30, 2008; U.S. Provisional Patent Application Ser. No. 61/057,797, entitled "Reduced-Pressure, Compression System and Apparatus for use on Breast Tissue," filed May 30, 2008; U.S. Provisional Patent Application Ser. No. 61/057,805, entitled "Super-Absorbent, Reduced-Pressure Wound Dressing and System," filed May 30, 2008; U.S. Provisional Patent Application Ser. No. 61/057,810, entitled "Reduced-Pressure, Compression System and Apparatus for use on a Joint," filed May 30, 2008; U.S. Provisional Patent Application Ser. No. 61/121,362, entitled "Reduced-Pressure Wound treatment System Employing an Anisotropic Drape," filed Dec. 10, 2008; and U.S. Provisional Patent Application Ser. No. 61/144,067, entitled "Reduced-Pressure, Compression System and Apparatus for use on a Joint," filed Jan. 12, 2009. All of these provisional applications are incorporated herein by reference for all purposes.

BACKGROUND

The present invention relates generally to medical treatment systems, and more particularly, to super-absorbent, reduced-pressure wound dressings and systems suitable for use with wounds such as surgical wounds.

Physicians perform millions of surgical procedures each year around the world. Many of the procedures are performed as open surgery and an increasing number are performed using minimally invasive surgery, such as endoscopic, arthroscopic, and laparoscopic procedures. As one example, the American Society for Aesthetic Plastic Surgery reports that there were more than 450,000 liposuction procedures in the United States in 2007.

Surgical procedures involve acute wounds, e.g., an incision, in the epidermis and related tissue. In many instances, the incision is closed at the conclusion of the procedure using a mechanical apparatus, such as staples or suture, or closed using adhesives. Thereafter, the wound is often merely covered with a dry, sterile bandage. Of course, there is usually more disruption than just at the epidermis.

With many surgical procedures, particularly those done with minimally invasive techniques, much of the disruption or damage is below the epidermis, or at a subcutaneous level. Again, as one example, in one type of liposuction procedure, after the introduction of a tumescent fluid (saline, mild painkiller, and epinephrine), the surgeon will use a trocar and cannula with suction to remove fatty areas. In doing so, it is not uncommon to have subcutaneous voids and other tissue defects formed at tissue sites remote from the incision through which the cannula was placed or other incisions through which equipment was placed. The damaged tissue will need time and care to heal and poses a number of potential complications and risks including edema, seroma, hematoma, further bruising, and ecchymosis to name some.

To facilitate healing after many surgical procedures, such as liposuction, depending on the body part involved, a firm-fitting wrap or elastic compression garment may be used for weeks on the patient. These devices are at times uncomfortable, may apply compression in a non-uniform manner, and can be difficult to take off and put on. In addition, because of edema, a number of different compression garments may be required for a single patient. It would be desirable to address some or all of the shortcomings of post-surgical wound care at the incision and at the undermined subcutaneous tissue.

BRIEF SUMMARY

The illustrative embodiments herein may be used with wounds, or irregular tissue, including area wounds and linear wounds. "Linear wound" refers generally to a laceration or incision whether in a line or not. According to an illustrative embodiment, a dressing assembly for use with a reduced-pressure treatment system includes a breathable, fluid restricted dry layer for placement against a wound on a patient and having a first surface and a second, inward-facing surface. The dressing assembly further includes a super-absorbent layer having a first surface and second, inward-facing surface. The second, inward-facing surface of the super-absorbent layer is disposed adjacent to the first surface of the breathable dry layer. The dressing assembly further includes a non-breathable layer having a first surface and a second, inward-facing surface. The second, inward-facing surface of the non-breathable layer is disposed adjacent to the first surface of the super-absorbent layer.

According to one illustrative embodiment, a reduced-pressure treatment system for treating a wound includes a super-absorbent bolster for placing on the patient's epidermis and substantially sized to overlay the wound. The super-absorbent bolster is operable to manifold reduced pressure. The reduced-pressure treatment system further includes a sealing subsystem for providing a fluid seal between the super-absorbent dressing bolster and the patient and a reduced-pressure subsystem for delivering reduced pressure to the sealing subsystem. The sealing subsystem and reduced-pressure subsystem are operable to deliver reduced pressure to the wound. The super-absorbent dressing bolster, sealing subsystem, and reduced-pressure subsystem are operable to develop a compressive force.

According to one illustrative embodiment, a system for assisting the healing of a wound on a patient includes a super-absorbent bolster assembly for placing on the wound of the patient, a sealing subsystem for providing a fluid seal over the super-absorbent bolster assembly and the patient, and a reduced-pressure subsystem for delivering a reduced pressure to the sealing subsystem. The super-absorbent bolster, sealing subsystem, and reduce-pressure subsystem are operable to deliver reduced pressure to the wound and remove exudate from the wound. The super-absorbent bolster may be operable to hold more than 250 milliliters of fluid while presenting a dry, inward-facing surface. The absorbent bolster assembly includes a breathable, fluid restricted dry layer having a first surface and a second, inward-facing surface and a super-absorbent layer having a first surface and second, inward-facing surface. The second, inward-facing surface of the super-absorbent layer is disposed adjacent to the first surface of the breathable dry layer.

Other objects, features, and advantages of the illustrative embodiments will become apparent with reference to the drawings and the detailed description that follow.

BRIEF DESCRIPTION OF THE DRAWINGS

A more complete understanding of the present invention may be obtained by reference to the following Detailed Description when taken in conjunction with the accompanying Drawings wherein.

DETAILED DESCRIPTION

In the following detailed description of the preferred embodiments, reference is made to the accompanying drawings that form a part hereof, and in which is shown, by way of illustration, specific embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
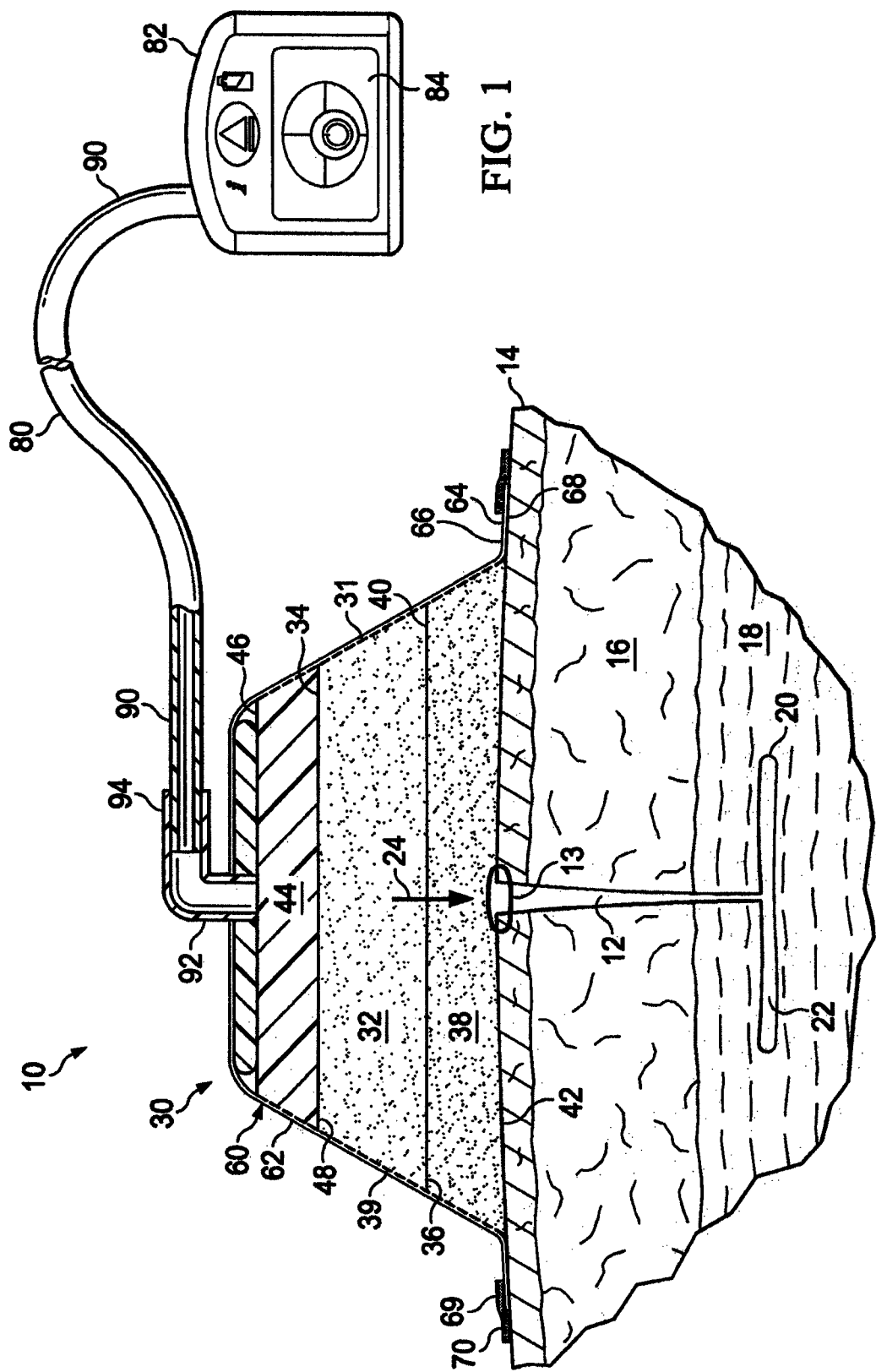
FIG. 1 is a schematic, cross-section (with a portion shown in elevation view) of an illustrative embodiment of a reduced-pressure treatment system for treating a wound.

Referring to FIG. 1, an illustrative embodiment of a reduced-pressure treatment system 10 for treating a wound, e.g., a linear wound, is presented. With the system 10, exudate and fluids are held by a dressing bolster to an extent that a portable reduced-pressure source may not need a storage canister. The system 10 may develop a compression force that is applied against a portion of the patient and that may be controlled in real time. The system 10 may be used with linear wounds 12 (e.g., an incision), area wounds, grafts, or subcutaneous voids. Among other things, when applied, the system 10 may help stabilize or hold tissue, enhance tensile strength of a wound, compress subcutaneous tissue to help reduce dead space, isolate the wound from external infectious sources, or enhance perfusion. Tensile strength of the wound means the strength of the wound as a force attempts to pull the wound apart or open. Unless otherwise indicated, as used herein, "or" does not require mutual exclusivity.

The reduced-pressure treatment system 10 is shown in the region of the linear wound 12, which is an incision through epidermis 14 and dermis 16 and reaching into a hypodermis or subcutaneous tissue 18. The subcutaneous tissue 18 may include numerous tissue types such as fatty tissue or muscle. An undermined subcutaneous tissue 20 is shown extending out from the linear wound 12 and includes, in this instance, a subcutaneous defect, dead space, or void 22. The undermined subcutaneous tissue 20 is often caused by surgical procedures such as liposuction. The undermined subcutaneous tissue 20 may include voids (such as void 22), open spaces, and various defects that can be troublesome for a number of reasons such as allowing fluids to build that may result in edema.

The linear wound 12 may be closed using any closing device such as staples, sutures, or adhesive, but is shown in this embodiment with suture 13. The reduced-pressure treatment system 10 is for treating a linear wound, such as linear wound 12, which is an incision in this illustration. The reduced-pressure treatment system may also be used to treat the subcutaneous tissue 20, an area wound, or a graft.

The reduced-pressure treatment system 10 includes a super-absorbent dressing assembly 30, which includes a super-absorbent dressing bolster 31; a sealing subsystem 60; and a reduced-pressure subsystem 80. When reduced pressure is supplied to the super-absorbent dressing bolster 31, the super-absorbent dressing bolster 31 distributes the reduced pressure to the linear wound 12, develops a compressive force 24, removes fluid, such as exudate, from the linear wound 12, and substantially holds (or stores) all the removed fluid. The reduced-pressure system 10 is operable to deliver reduced pressure to the linear wound 12 that is realized at the level of the subcutaneous tissue 22 and helps approximate—bring together—the tissues in that region as well as helping to remove any air or any other fluids.

The super-absorbent dressing assembly 30 includes a super-absorbent bolster 31 having a super-absorbent layer 32, which has a first surface 34 and a second, inward-facing surface 36; an entry layer 38 (or fluid entry layer), which has a first surface 40 and a second, inward-facing surface 42, and which may be a breathable, fluid restricted dry layer for placement against the linear wound 12; and a top layer 44, which has a first surface 46 and a second, inward-facing surface 48, and which may be a non-breathable layer. The super-absorbent dressing bolster 31 is sized and shaped to substantially extend over the linear wound 12, and if used in an area application, the super-absorbent dressing bolster 31 is sized to substantially match the estimated area of undermined subcutaneous tissue 20 although a larger or smaller size may be used in different applications. The super-absorbent layer 32 is further described below.

"Breathable" as used herein means gas permeable. The breathable, fluid restricted dry layer allow a gas to permeate and restricts fluid as will be described. That the breathable, fluid restricted dry layer is "fluid restricted" means that it allows fluid to enter, e.g. exudate from the wound may pass through the layer, but the liquid does not generally flow the other direction. This means that the bottom surface of the breathable, fluid restricted dry layer remains dry to the touch. The breathable, fluid restricted dry layer is analogous to the layer of a typical disposable diaper that is next to a baby's skin.

The super-absorbent dressing bolster 31 is operable to distribute reduced pressure to the linear wound 12 and develop forces. The term "manifold" as used herein generally refers to a substance or structure that is provided to assist in applying reduced pressure to, delivering fluids to, or removing fluids from a tissue site. A manifold typically includes a plurality of flow channels or pathways that are interconnected to improve distribution of fluids provided to and removed from the area of tissue around the manifold.

The sealing subsystem 60 includes a drape 62, or sealing member. The drape 62 may be any material that provides a fluid seal, such as an elastomeric material. "Fluid seal," or "seal," means a seal adequate to hold reduced pressure at a desired site given the particular reduced-pressure subsystem involved. "Elastomeric" means having the properties of an elastomer. It generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of the drape materials include a silicone drape, 3M Tegaderm drape, acrylic drape such as ones available from Avery Dennison, or an incise drape.

The drape 62 may be coupled to the super-absorbent dressing bolster 31 and in particular to the first surface 46 of the top layer 44. The coupling may occur in many ways. The drape 62 and the top layer 44 may be coupled using adhesives such as by acrylic adhesive, silicone adhesive, hydrogel, hydrocolloid, etc. The drape 62 and the top layer 44 may be bonded by heat bonding, ultrasonic bonding, and radio frequency bonding, etc. The coupling may occur in patterns, more completely, or totally. Structural members may be added to the bond to make the drape 62 behave anisotropically in a desired direction, i.e. to make an anisotropic drape material. The anisotropic drape material helps the dressing assembly 30 to primarily move in a given direction, i.e. only about a certain axis or axes.

In the embodiment of FIG. 1, the drape 62 is sized to extend beyond a peripheral edge 39 of the super-absorbent dressing bolster 31 and thereby to form a drape extension 64. The drape extension 64 has a first surface 66 and a second, inward-facing surface 68. The drape 62 may be sealed against the patient's epidermis 14 using a sealing apparatus 69 for providing a fluid seal, which allows a reduced pressure to be maintained by the reduced-pressure subsystem 80. The sealing apparatus 69 may take numerous forms such as adhesive, a sealing tape 70, or drape tape or strip, double-side drape tape, paste, hydrocolloid, hydrogel, or other sealing means. If a tape 70 is used, the tape 70 may be formed of the same material as the drape 62 with a pre-applied, pressure-sensitive adhesive. In another embodiment, a pressure sensitive adhesive may be applied on the second surface 68 of the drape extension 64. The adhesive provides a substantially fluid seal between the drape 62 and the epidermis 14 of the patient. Before the drape 62 is secured to the patient, the adhesive may have removable strips covering the pressure-sensitive adhesive. In using the tape 70, the tape 70 is applied over the extension 64 to provide a fluid seal.

The reduced-pressure subsystem 80 includes a reduced-pressure source 82, which can take many different embodiments that provide a reduced pressure as a part of the reduced-pressure treatment system 10. The reduced-pressure source 82 may be any device for supplying a reduced-pressure, such as a vacuum pump, wall suction, or other source. While the amount and nature of reduced-pressure applied to a tissue site will typically vary according to the application, the reduced-pressure will typically be between −5 mm Hg and −500 mm Hg and more typically between −100 mm Hg and −300 mm Hg. A pressure of −200 mm Hg may be used in some situations.

As used herein, "reduced-pressure" generally refers to a pressure less than the ambient pressure at a tissue site that is being subjected to treatment. In most cases, this reduced-pressure will be less than the atmospheric pressure at which the patient is located. Alternatively, the reduced-pressure may be less than a hydrostatic pressure at the tissue site. Unless otherwise indicated, values of pressure stated herein are gauge pressures. The reduced-pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced-pressure or vacuum pressure typically refers to a relative reduction in absolute pressure.

In order to maximize patient mobility and ease, the reduced-pressure source 82 may be a battery-powered, single-use reduced-pressure generator, or therapy unit. Such a pressure source 82 facilitates application in the operating room and provides mobility and convenience for the patient during the rehabilitation phase. Other sources of reduced pressure may be utilized such as V.A.C.® therapy unit, which is available from KCI of San Antonio, Tex., or a wall suction unit. The reduced-pressure source could also be supplied by a portable mechanical device, such as a piston in a tube, depending on how much leakage there is with the fluid seal between the dressing bolster and the epidermis.

The super-absorbent nature of the super-absorbent dressing bolster 31 allows for the possibility of utilizing a reduced-pressure source that does not require a remote fluid-storage canister because the super-absorbent dressing bolster 31 effectively stores the fluid. The super-absorbent layer 32 may hold 300 milliliters of fluid or more. At the same time, entry layer 38 keeps the fluid away from the patient's epidermis 14 so that maceration may be avoided. The reduced-pressure source 82 is shown having a battery compartment 84. An interposed membrane filter, such as hydrophobic or oleophobic filter, may be interspersed between a reduced-pressure delivery conduit, or tubing, 90 and the reduced-pressure source 82.

The reduced pressure developed by the reduced-pressure source 82 is delivered through the reduced-pressure conduit 90 to a reduced-pressure interface 92, which may be an elbow port 94. In one embodiment, the elbow port 94 is a TRAC® technology port available from KCI of San Antonio, Tex. The reduced-pressure interface 92 allows reduced pressure to be delivered to the sealing subsystem 60 and realized within an interior portion of sealing subsystem 60. In this particular embodiment, the reduced-pressure interface 92 extends through the drape 62 and into the super-absorbent dressing bolster 31.

In operation, the reduced-pressure treatment system 10 may be applied in the operating room after a surgical procedure on the patient or elsewhere. The second surface 42 of the entry layer 38 of the super-absorbent dressing bolster 31 would be placed against the patient's epidermis 14 over the linear wound 12. The dressing assembly 30 may be sized for typical application involved in the procedure performed by a healthcare provider. The dressing assembly 30 may be sized, shaped, and configured to work in different anatomical applications such as abdomen, chest, thighs, hip, etc.

If the drape 62 is not already coupled to the super-absorbent dressing bolster 31, the drape 62 is placed over the first surface 46 of the top layer 44 and the peripheral edge 39 of the super-absorbent dressing bolster 31 with an extra portion extending beyond the peripheral edge 39 to form the drape extension 64. The drape extension 64 can then be taped down with the tape 70 or an adhesive used to form a fluid seal between the drape 62 and the patient's epidermis 14. The fluid seal need only be adequate to allow the reduced-pressure treatment system 10 to maintain a reduced pressure on the treatment area or tissue site for a desired treatment time. The reduced-pressure interface 92 is applied if not already installed. The reduced-pressure delivery conduit 90 is fluidly coupled to the reduced-pressure source 82 and the reduced-pressure interface 92. The reduced-pressure source 82 may then be activated and a reduced pressure delivered to the super-absorbent dressing bolster 31.

As the pressure is reduced at the super-absorbent dressing bolster 31, the reduced pressure is transmitted further still through the super-absorbent dressing bolster 31 so that the reduced pressure is experienced at the patient's epidermis 14 proximate the linear wound 12. At least at the early stages of the healing process, the reduced pressure may be realized through the linear wound 12 and into the subcutaneous tissue 20 and, if so, the reduced pressure helps close defects (if any) such as the subcutaneous void 22 and generally provides stability to the treatment area. The reduced pressure delivered to the super-absorbent dressing bolster 31 also develops a compressive force 24 that again provides stability and may enhance tensile strength, etc. The compressive force 24 may be more than just at the top of the epidermis 14. The compressive force may extend down deeper and may be experienced at the level of the subcutaneous tissue 20.

During treatment, care is taken to avoid skin irritation, such as blistering of the patient's epidermis 14, due to secondary shear, secondary strain or other effects. To help avoid skin irritation, the peripheral edge 39 may be shaped or angled or an inner layer may be added between the super-absorbent dressing bolster 31 and the patient's epidermis 14.

Figure 2:
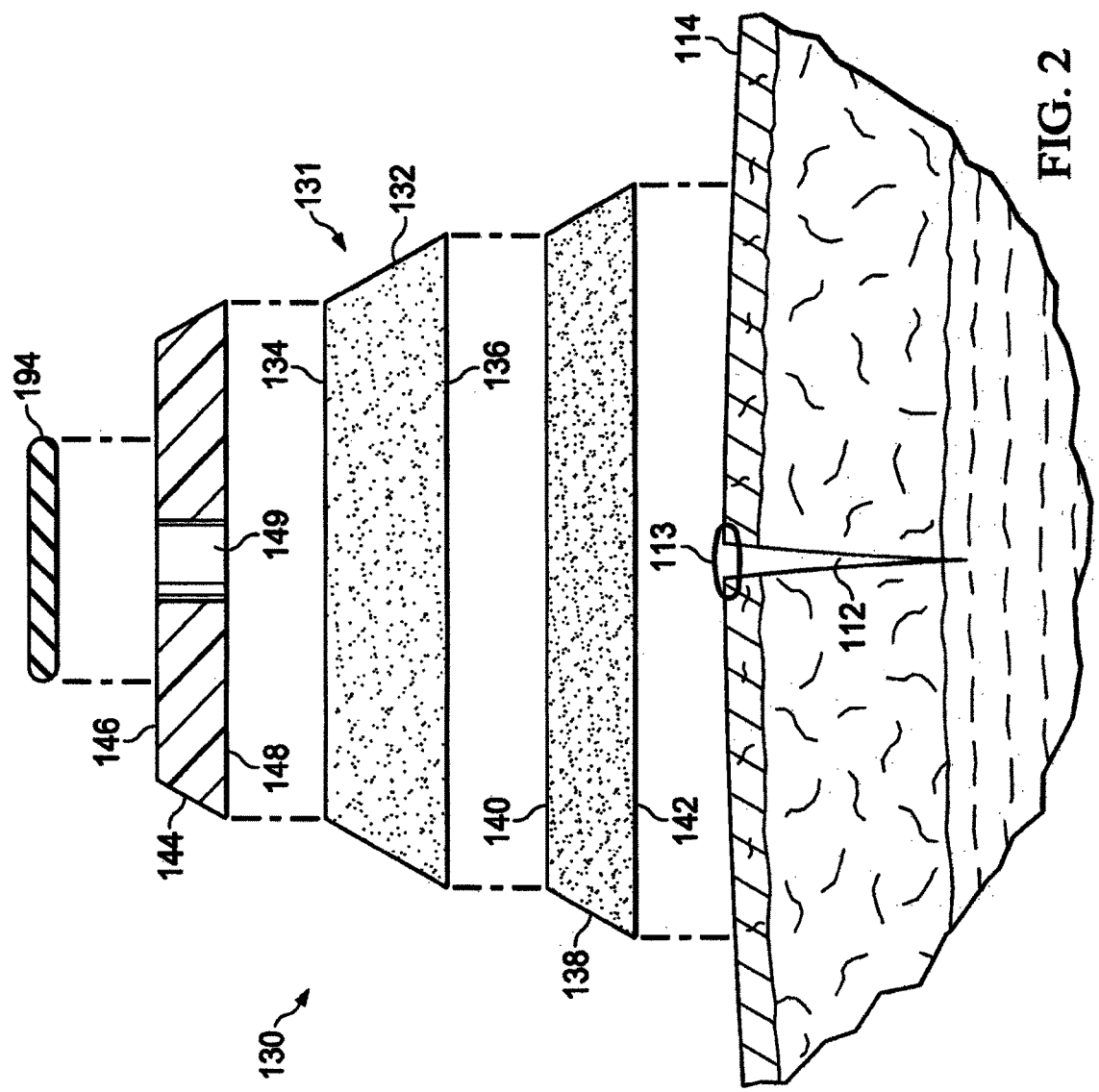
FIG. 2 is an exploded schematic, cross-section of an illustrative embodiment of a dressing assembly for use with a reduced-pressure wound treatment system.

Referring now to FIG. 2, an exploded, schematic cross-section of a portion of a super-absorbent dressing assembly 130 for use with a reduced-pressure wound treatment system is shown. The super-absorbent dressing assembly 130 is analogous in most respect to the super-absorbent dressing assembly 30 of FIG. 1, but the super-absorbent dressing assembly 130 is shown without a drape extending over the super-absorbent dressing assembly 130. The super-absorbent dressing assembly 130 may include a number of layers, but is shown in this illustrative embodiment as having a super-absorbent dressing bolster 131 that includes three main layers: a super-absorbent layer 132, an entry layer 138, and a top layer 144.

The entry layer 138 has a first surface 140 and a second, inward-facing surface 142. The entry layer 138 is intended to allow fluid to leave a linear wound 112 on the patient's epidermis 114 and pass through the entry layer 138, but not remain on the epidermis 114. In other words, the entry layer 138 functions to effectively allow flow in only one direction. This one-way action helps to avoid maceration of the epidermis 114. The entry layer 138 also helps manifold, or distribute, reduced pressure to the linear wound 112. The entry layer 138 may be described as a breathable dry layer. Many materials may be used for the entry layer 138 such as a hydrophilic non-woven material.

The top layer 144 has a first surface 146 and a second, inward-facing surface 148. The top layer 144 may be a non-breathable layer. The top layer 144 may have an aperture 149 formed through the top layer 144 to accommodate a reduced-pressure fluidly coupled to a reduced-pressure source. The top layer 144 helps provide a seal over the super-absorbent layer 132. A number of materials may be used for the top layer 144 such as a polyethylene film that will keep fluids from leaking out. In an alternative embodiment, the top layer 144 may be omitted and a drape alone used to contain fluids within the super-absorbent dressing assembly 130.

An additional interface breathable layer 194 may added on the first surface 146 of the top layer 144 to function as a filter. The interface breathable layer 194 covers aperture 149. The interface breathable layer 194 allows delivery of reduced pressure and prevents portions of the super-absorbent layer 132 from entering the reduced-pressure interface, e.g., reduced-pressure interface 92 of FIG. 1, that rests on top of the super-absorbent dressing assembly 130.

The super-absorbent layer 132 has a first surface 134 and a second, inward-facing surface 136. The super-absorbent layer 132 helps manifold reduced pressure to the entry layer 138 and on to the linear wound 112. The super-absorbent layer 132 is operable to hold relatively large quantities of fluid and is operable to help serve as a dressing bolster for developing a compressive force (e.g., force 24 in FIG. 1).

The super-absorbent layer 32 (FIG. 1) and the super-absorbent layer 132 may be formed from superabsorbent polymers (SAP) of the type often referred to as "hydrogels," "super-absorbents," or "hydrocolloids." Super-absorbent spheres may be used as well that would manifold reduced pressure until the super-absorbent spheres become saturated. In order to allow a reduced pressure to be used without a remote canister or with a relatively small remote canister in a human patient, it is desirable with many surgical applications to make the super-absorbent layer 132 operable to hold at least 300 milliliters of fluid. It some applications, it may additionally be desirable to provide super-absorbent material in the reduced-pressure deliver conduit (e.g., 90 in FIG. 1) between the super-absorbent dressing 132 and the reduced-pressure source to further hold fluid.

When fluid is added to the super-absorbent layer 132, the dressing bolster 131 becomes more rigid and under reduced pressure this results in an increased compressive force, such as force 24 in FIG. 1. The fluid may come in the form of exudates or other fluids from the linear wound 112 or may be a supplied fluid, such as a saline, that is intentionally added by injection or otherwise.

Figure 3:
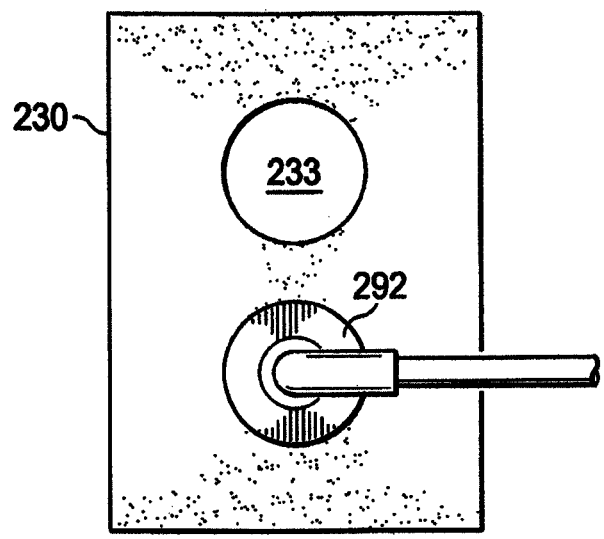
FIG. 3 is schematic, top view of a portion of illustrative embodiment of a dressing assembly for use with a reduced-pressure wound treatment system.

Referring now to FIG. 3, a super-absorbent dressing assembly 230 may be formed with a reduced-pressure interface 292 for delivering reduced pressure and an injection port 233. The injection port 233 facilitates injection of a fluid into a super-absorbent layer of the super-absorbent dressing assembly 230.

Figure 4:
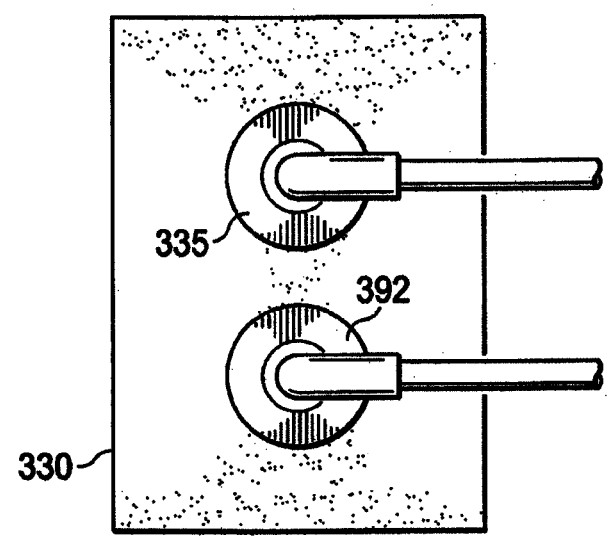
FIG. 4 is schematic, top view of a portion of another illustrative embodiment of a dressing assembly for use with a reduced-pressure wound treatment system.

Referring now to FIG. 4, a super-absorbent dressing assembly 330 may have a first interface 392, or reduced-pressure interface, for delivering a reduced pressure to a super-absorbent layer, and may also include a second interface 335, or a fluid delivery interface, for delivering a fluid, such as saline, to the super-absorbent layer.

Whether by an injection port 233 (FIG. 3) or a second interface 335 (FIG. 4) or another means, fluid may be added to the super-absorbent layer to increase the rigidity of the super-absorbent layer and this provides a liquid-controlled bolster. The addition of liquid controls the rigidity which in turn can control the compressive force developed under reduced pressure. If the fluid is supplied from a exudating (e.g., bleeding) wound, the additional compressive force developed with additional fluid—exudate—helps make the dressing somewhat self-adjusting or self-regulating. This may be particularly useful in wound treatment on the battlefield. The amount of compression developed may also be influenced by the elasticity of the drape; the more stretchable it is, the less compressive force will be developed. A transducer and controller may be provided that facilitates measurement of the compression force and is able to adjust the quantity of fluid supplied through the second interface 335 (or remove through the first interface 392) to regulate the compression at a desired level or within desired parameters.

According to another illustrative embodiment, a method of manufacturing a dressing assembly for use with a reduced-pressure wound treatment system includes the steps of: forming a breathable, fluid restricted dry layer for placement against a wound and having a first surface and a second, inward-facing surface; disposing a super-absorbent layer having a first surface and second, inward-facing surface adjacent to the breathable dry layer; disposing a non-breathable layer having a first surface and a second, inward-facing surface adjacent to the first surface of the super-absorbent layer. The method of manufacturing further includes placing a drape over the first surface of the non-breathable layer; and fluidly coupling a reduced-pressure interface to the super-absorbent layer.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A dressing bolster, comprising:
    a fluid-restricted dry layer configured to be placed against a tissue site;
    a super-absorbent layer adjacent to the fluid-restricted dry layer, the super-absorbent layer configured to receive and store fluid and configured to become more rigid with an addition of fluid;
    a non-breathable layer adjacent the super-absorbent layer and opposite the fluid-restricted dry layer; and
    a drape configured to extend over the super-absorbent layer;
    wherein the non-breathable layer is configured to be disposed between the super-absorbent layer and the drape; and
    wherein the dressing bolster is configured to develop a compressive force on the tissue site.

2. The dressing bolster of claim 1, further comprising a reduced-pressure interface configured to be fluidly coupled to the super-absorbent layer and operable to receive reduced pressure.

3. The dressing bolster of claim 1, wherein the compressive force is controlled in real-time.

4. The dressing bolster of claim 1, wherein a bond coupling the drape and the non-breathable layer comprises structural members configured to make the drape behave anisotropically.

5. The dressing bolster of claim 1, wherein the fluid-restricted dry layer comprises a hydrophilic non-woven material.

6. The dressing bolster of claim 2, wherein the non-breathable layer has an aperture adapted to accommodate a reduced pressure in fluid communication with the reduced-pressure interface.

7. The dressing bolster of claim 1, further comprising an interface breathable layer configured to be disposed adjacent to the non-breathable layer opposite the super-absorbent layer.

8. The dressing bolster of claim 6, further comprising:
    an interface, breathable layer configured to be disposed adjacent to the non-breathable layer;
    wherein the interface, breathable layer is configured to cover the aperture and to allow delivery of reduced pressure and prevent super-absorbent layer material from entering the reduced-pressure interface.

9. A dressing assembly, comprising:
    a fluid-restricted dry layer configured to be placed adjacent a tissue site and to restrict fluid communication through the fluid-restricted dry layer in one direction;
    a super-absorbent layer configured to be coupled to the fluid-restricted dry layer and configured to receive and store fluid;
    a non-breathable layer configured to be disposed adjacent to the super-absorbent layer and opposite the fluid-restricted dry layer;
    a drape configured to extend over the non-breathable layer; and
    wherein the non-breathable layer is configured to be disposed between the superabsorbent layer and the drape.

10. The dressing assembly of claim 9, further comprising a drape extension formed by a portion of the drape extending beyond a peripheral edge of the fluid-restricted dry layer, super-absorbent layer, and non-breathable layer.

11. The dressing assembly of claim 9, wherein the super-absorbent layer comprises superabsorbent polymers.

12. The dressing assembly of claim 9, wherein the fluid-restricted dry layer is gas permeable.

13. The dressing assembly of claim 9, further comprising an injection port configured to be fluidly coupled to the super-absorbent layer and adapted to deliver fluid to the super-absorbent layer.

14. The dressing assembly of claim 9, wherein the fluid-restricted dry layer and the super-absorbent layer each comprise an angled peripheral edge.

15. The dressing assembly of claim 9, wherein the super-absorbent layer is configured to become more rigid with an addition of fluid.

16. A reduced-pressure treatment system, comprising:
    a fluid-restricted dry layer configured to be placed against a tissue site;
    a super-absorbent layer configured to:
        be disposed adjacent to the fluid-restricted dry layer,
        receive fluid from the fluid-restricted dry layer,
        store the received fluid, and
        increase rigidity with an addition of fluid;
    a non-breathable layer configured to be disposed adjacent to the super-absorbent layer and opposite the fluid-restricted dry layer;
    a drape configured to be disposed adjacent to the non-breathable layer;
    wherein the non-breathable layer is configured to be disposed between the superabsorbent layer and the drape; and a reduced-pressure subsystem configured to be in fluid communication with the super-absorbent layer.

17. The reduced-pressure treatment system of claim 16, further comprising a sealing apparatus for providing a fluid seal between an epidermis and the drape.

18. The reduced-pressure treatment system of claim 16, wherein the super-absorbent layer is configured to develop a compressive force on the tissue site.

19. The reduced-pressure treatment system of claim 18, wherein the compressive force is greater with an addition of fluid to the super-absorbent layer.

20. The reduced-pressure treatment system of claim 16, wherein the fluid-restricted dry layer is configured to restrict fluid communication through the fluid-restricted dry layer in one direction.

\* \* \* \* \*

UNITED STATES PATENT AND TRADEMARK OFFICE
CERTIFICATE OF CORRECTION

PATENT NO. : 10,695,225 B2  
APPLICATION NO. : 14/309705  
DATED : June 30, 2020  
INVENTOR(S) : Larry Tab Randolph et al.

Page 1 of 1

It is certified that error appears in the above-identified patent and that said Letters Patent is hereby corrected as shown below:

On the Title Page

<u>On Page 3, Column 2, under (item (56) Other Publications)</u>  
Line 1, delete "correspdonding" and insert -- corresponding --, therefor.  
Line 5, delete "Modem" and insert -- Modern --, therefor.

<u>On Page 4, Column 1, Under (item (56) Other Publications)</u>  
Line 1, delete "Bjöm" and insert -- Björn --, therefor.

<u>On Page 4, Column 2, Under (item (56) Other Publications)</u>  
Line 6, delete "Hypermia" and insert -- Hyperemia --, therefor.

In the Specification

<u>Column 5</u>  
Line 23, delete "Tegaderm" and insert -- Tegaderm® --, therefor.

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*